United States Patent
Fomsgaard (10) Patent No.: US 10,729,765 B2
(45) Date of Patent: Aug. 4, 2020

(54) ALPHA-TOCOPHEROL-BASED ADJUVANTED SOLVENT FOR DNA VACCINES

(71) Applicant: Statens Serum Institut, Copenhagen S (DK)

(72) Inventor: Anders Fomsgaard, Copenhagen K (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 15/512,158

(22) PCT Filed: Sep. 17, 2015

(86) PCT No.: PCT/DK2015/050279
§ 371 (c)(1),
(2) Date: Mar. 17, 2017

(87) PCT Pub. No.: WO2016/041562
PCT Pub. Date: Mar. 24, 2016

(65) Prior Publication Data
US 2017/0246295 A1    Aug. 31, 2017

(30) Foreign Application Priority Data
Sep. 19, 2014 (DK) .................. 2014 00534

(51) Int. Cl.
| | | |
|---|---|---|
| *A61K 39/39* | (2006.01) | |
| *A61K 45/06* | (2006.01) | |
| *A61K 39/145* | (2006.01) | |
| *C12N 7/00* | (2006.01) | |
| *A61K 9/00* | (2006.01) | |
| *C07D 311/72* | (2006.01) | |
| *A61K 9/107* | (2006.01) | |
| *A61K 31/355* | (2006.01) | |
| *A61K 47/22* | (2006.01) | |
| *A61K 39/00* | (2006.01) | |

(52) U.S. Cl.
CPC ............ *A61K 39/39* (2013.01); *A61K 9/0019* (2013.01); *A61K 9/107* (2013.01); *A61K 31/355* (2013.01); *A61K 39/145* (2013.01); *A61K 45/06* (2013.01); *A61K 47/22* (2013.01); *C07D 311/72* (2013.01); *C12N 7/00* (2013.01); *A61K 2039/53* (2013.01); *A61K 2039/54* (2013.01); *A61K 2039/55511* (2013.01); *A61K 2039/55566* (2013.01); *C12N 2760/16134* (2013.01)

(58) Field of Classification Search
None
See application file for complete search history.

(56) References Cited

U.S. PATENT DOCUMENTS 7,943,377 B2    5/2011 Carnes et al.
2008/0132580 A1*  6/2008 Mandavilli .......... A61K 9/7015
                                                  514/725

OTHER PUBLICATIONS

Toke et al., Exploitation of Langerhans cells for in vivo DNA vaccine delivery into the lymph nodes, 2014, Gene Therapy, vol. 21, pp. 566-574.*
Coudeville, et al., "Relationship between haemagglutination-inhibiting antibody titres and clinical protection against influenza: development and application of a bayesian random-effects model," Mar. 8, 2010, BMC Medical Research Methodology, 10:18:1-11.
Durando, et al., "Adjuvants and alternative routes of administration towards the development of the ideal influenza vaccine," Jan. 1, 2011, Human Vaccines, 7:sup1, 29-40.
European Medicines Agency, Science Medicines Health, "EMA/CVMP/1071/2011," 'Discussion for the approval of Porcilis Porcoli Diluvac Forte,' Jun. 30, 2011.
Gorres, et al., "DNA Vaccination Elicits Protective Immune Responses against Pandemic and Classic Swine Influenza Viruses in Pigs," Sep. 14, 2011, Clinical and Vaccine Immunology, vol. 18, No. 11, pp. 1987-1995.
Graham, et al., DNA Vaccine Delivered by a Needle-Free Injection Device Improves Potency of Priming for Antibody and CD8+ T-Cell Responses after rAd5 Boost in a Randomized Clinical Trial, Apr. 8, 2013, PLoS One, 8(4): e59340 (11 pages).
Jalilian, et al., "Properties and prospects of adjuvants in influenza vaccination—messy precipitates or blessed opportunities?," Nov. 6, 2013, Molecular and Cellular Therapies, 1:2 (16 pages).
Kutzler, et al., "DNA vaccines: ready for prime time?," Oct. 2008, Nature Reviews, Genetics, vol. 9, pp. 776-788.
World Health Organization, "Influenza vaccine viruses and reagents," www.who.int/influenza/vaccines/virus/en/, Aug. 3, 2014 printout via web.archive.org, 3 pages.
Williams, "Vector Design for Improved DNA Vaccine Efficacy, Safety and Production," Vaccines, Jun. 25, 2013, Vaccines, pp. 225-249.
Al-Thamir, et al., Investigation the Immunoadjuvant Activity for Polysorbate 80, Asian J. of Pharmacy, Nursing and Medical Sciences, Jun. 2013, vol. 1, Issue 1, pp. 18-24.
Bragstad, et al., A polyvalent influenza A DNA vaccine induces heterologous immunity and protects pigs against pandemic A(H1N1)pdm09 virus infection, Vaccine, Apr. 26, 2013, published online Mar. 13, 2013, 31(1):2281-2288.
Ferrari, et al., Evaluation of the immune response induced by intradermal vaccination by using a needle-less system in comparison with the intramuscular route in conventional pigs, Res. Vet. Sci., Feb. 2011, published online May 23, 2010, 90(1):64-71.
Garcon, et al., Development and evaluation of AS03, an Adjuvant System containing α-tocopherol and squalene in an oil-in-water emulsion, Expert Rev Vaccines, Mar. 2012, 11(3):349-66, Abstract Only.

(Continued)

*Primary Examiner* — Benjamin P Blumel
(74) *Attorney, Agent, or Firm* — Duminiak Law, LLC (57) ABSTRACT

The present invention discloses a delivery system for nucleic acid vaccines comprising an emulsion of tocol and esters hereof. Vaccines and new ways of administration of DNA vaccines are disclosed.

11 Claims, 5 Drawing Sheets

Specification includes a Sequence Listing.

(56) References Cited

OTHER PUBLICATIONS

Roman, et al., Immunogenicity and safety in adults of one dose of influenza A H1N1v 2009 vaccine formulated with and without AS03A-adjuvant: preliminary report of an observer-blind, randomised trial, Vaccine, Feb. 17, 2010, published online Dec. 22, 2019, 28(7):1740-5, Abstract Only.

Visser, et al., Vaccination strategies for improving the efficacy of programs to eradicate Aujeszky's disease virus, Veterinary Microbiology, Apr. 1997, 55:61-74.

* cited by examiner

SEQUENCE LISTING

<160> NUMBER OF SEQ ID NOS: 6

<210> SEQ ID NO 1
<211> LENGTH: 1497
<212> TYPE: DNA
<213> ORGANISM: Influenza A virus

<400> SEQUENCE: 1

```
atggccagcc agggcaccaa gagaagctac gagcagatgg aaaccgacgg cgagaggcag      60
aacgccaccg agatcagggc cagcgtgggc aggatgatcg gcggcatcgg caggttctac     120
atccagatgt gcaccgagct gaagctgtcc gactacgagg gcaggctgat ccagaacagc     180
atcaccatcg agaggatggt gctgtccgcc ttcgacgaga gaagaaacaa gtacctggaa     240
gagcacccca gcgccggcaa ggaccccaag aaaaccggcg gacccatcta cagaaggatc     300
gacggcaagt ggatgagaga gctgatcctg tacgacaagg aggaaatcag aaggatctgg     360
cggcaggcca acaacggcga ggacgccaca gccggcctga cccacatgat gatctggcac     420
agcaacctga acgacgccac ctaccagagg accagggccc tcgtcagaac cggcatggac     480
ccccggatgt gcagcctgat gcagggcagc acactgccca gaagaagcgg agctgctgga     540
gccgccgtga agggcgtggg caccatggtg atggaactga tcaggatgat caagaggggc     600
atcaacgaca ggaacttttg gaggggcgag aacggcagaa ggaccaggat cgcctacgag     660
aggatgtgca acatcctgaa gggcaagttc cagacagccc cccagagggc catgatggac     720
caggtccggg agagcaggaa ccccggcaac gccgagatcg aggacctgat cttcctggcc     780
agaagcgccc tgatcctgag gggcagcgtg gcccacaaga gctgcctgcc cgcctgcgtg     840
tacggacccg ccgtggccag cggctacgac ttcgagagag agggctacag cctggtcggc     900
atcgacccct tcaggctgct gcagaactcc caggtgtact ctctgatcag gcccaacgag     960
aaccccgccc acaagtccca gctggtctgg atggcctgcc acagcgccgc cttcgaggat    1020
ctgagagtga gcagcttcat caggggcacc agagtggtgc ccaggggcaa gctgtccacc    1080
aggggcgtgc agatcgccag caacgagaac atggaaacca tggacagcag caccctggaa    1140
ctgagaagca ggtactgggc catcaggacc agaagcggcg gcaacaccaa ccagcagagg    1200
gccagcgccg gacagatcag cgtgcagccc accttctccg tgcagaggaa cctgcccttc    1260
gagagggcca ccatcatggc cgccttcacc ggcaacaccg agggcaggac cagcgacatg    1320
aggaccgaga tcatcagaat gatggaaagc gccaggcccg aggacgtgag cttccagggc    1380
```

-continued aggggcgtgt tcgagctgtc cgatgagaag gccacctccc ccatcgtgcc cagcttcgac 1440
atgagcaacg agggcagcta cttcttcggc gacaacgccg aggaatacga caactga 1497

<210> SEQ ID NO 2
<211> LENGTH: 988
<212> TYPE: DNA
<213> ORGANISM: Influenza A virus

<400> SEQUENCE: 2
atgagtcttt taaccgaggt cgaaacgtac gttctctcta tcgtcccgtc aggccccctc 60
aaagccgaga tcgcgcagag acttgaagat gtctttgcag ggaagaacac cgatcttgag 120
gctctcatgg aatggctaaa gacaagacca atcctgtcac ctctgactaa ggggatttta 180
ggatttgtgt tcacgctcac cgtgcccagt gagcgaggac tgcagcgtag acgctttgtc 240
caaaatgccc ttaatgggaa cggggatcca aataacatgg acagagcagt taaactgtac 300
aggaagctta agagggagat aacattccat ggggccaaag aagtagcact cagttattcc 360
gctggtgcac ttgccagttg tatgggcctc atatacaaca ggatggggac tgtgaccact 420
gaagtggcat ttggcctggt atgcgcaacc tgtgaacaga ttgctgattc ccagcatcgg 480
tctcacaggc aaatggtgac aacaaccaat ccactaatca gacatgagaa cagaatggta 540
ctggccagca ctacggctaa ggctatggag caaatggctg gatcgagtga gcaagcagca 600
gaggccatgg aggttgctag tcaggctagg caaatggtgc aggcgatgag aaccattggg 660
actcatccta gctccagtgc tggtctgaaa gacgatctta ttgaaaattt gcaggcctac 720
cagaaacgaa tgggggtgca gatgcaacga ttcaagtgat cctctcgtta ttgccgcaag 780
tatcattggg atcttgcact tgatattgtg gattcttgat cgtctttttt tcaaatgcat 840
ttatcgtcgc cttaaatacg gtttgaaaag agggccttct acggaaggag tgccggagtc 900
tatgagggaa gaatatcgaa aggaacagca gagtgctgtg gatgttgacg atggtcattt 960
tgtcaacata gagctggagt aaggcgcc 988

<210> SEQ ID NO 3
<211> LENGTH: 1723
<212> TYPE: DNA
<213> ORGANISM: Influenza A virus

<400> SEQUENCE: 3
atgaaggcta tcctggtggt gctgctgtac accttcgcca ccgccaacgc cgataccctg 60
tgcatcggct accacgccaa caacagcacc gacaccgtgg ataccgtgct ggaaaagaac 120
gtgaccgtga cccacagcgt gaacctgctg gaagataagc acaacggcaa gctgtgcaag 180
ctgagaggcg tggcccctct gcacctgggc aagtgcaata tcgccggctg gatcctgggc 240
aaccccgagt gcgagagcct gagcaccgcc agctcttggt cctacatcgt ggagacaccc 300
agcagcgaca acggcacctg ttaccccggc gacttcatcg actacgagga actgcgggag 360
cagctgtcca gcgtgtccag cttcgagcgg ttcgagatct tccccaagac cagctcctgg 420
cccaaccacg acagcaacaa gggcgtgacc gccgcctgtc ctcacgctgg ggccaagagc 480
ttctacaaga acctgatctg gctggtgaag aagggcaaca gctaccccaa gctgtccaag 540
agctacatca acgacaaggg caaagaggtg ctggtgctgt ggggcatcca ccaccctagc 600
accagcgccg accagcagag cctgtaccag aacgccgaca cctacgtgtt cgtgggcagc 660
agccggtaca gcaagaagtt caagcccgag atcgccatca gacccaaagt gcgggaccag 720
gaaggccgga tgaactacta ctggaccctg gtggagcccg gcgacaagat caccttcgag 780

```
gccaccggca atctggtggt gcccagatac gccttcgcca tggaaagaaa cgccggcagc      840
ggcatcatca tcagcgacac ccccgtgcac gactgcaaca ccacctgtca gacccccaag      900
ggggccatca acaccagcct gcccttccag aacatccacc ccatcaccat cggcaagtgc      960
cctaagtacg tgaagtccac caagctgaga ctggccaccg gctgcggaa catccccagc      1020 atccagagca gaggcctgtt cggggccatt gccggcttta tcgagggcgg ctggaccgga      1080
atggtggacg gtggtacgg ctaccaccac cagaatgagc agggcagcgg ctacgccgcc       1140
gacctgaagt ccacacagaa cgccatcgac gagatcacca caaagtgaa cagcgtgatc       1200 gagaagatga cacccagtt caccgccgtg ggcaaagagt caaccacct ggaaaagcgg        1260 atcgagaacc tgaacaagaa ggtggacgac ggcttcctgg acatctggac ctacaacgcc     1320
gagctgctgg tgctgctgga aaacgagcgg accctggact accacgactc caacgtgaag     1380
aatctgtacg agaaagtgcg gagccagctg aagaacaacg ccaaagagat cggcaacggc     1440
tgcttcgagt tctaccacaa gtgcgacaac acctgtatgg aaagcgtgaa gaacggcacc     1500
tacgactacc ccaagtacag cgaggaagcc aagctgaacc gggaagagat cgacggcgtg     1560
aagctggaaa gcacccggat ctaccagatc ctggccatct acagcaccgt ggccagctca     1620
ctggtcctgg tcgtgtccct gggcgctatc agcttctgga tgtgcagcaa cggcagcctg     1680
cagtgccgga tctgcatctg aggcgccgag aattcttaat taa                       1723
```

<210> SEQ ID NO 4
<211> LENGTH: 1432
<212> TYPE: DNA
<213> ORGANISM: Influenza A virus

<400> SEQUENCE: 4

```
atgaacccca accagaagat catcaccatc ggcagcgtgt gcatgaccat cggcatggcc       60
aacctgatcc tgcagatcgg caacatcatc agcatctgga tcagccacag catccagctg      120
ggcaaccaga accagatcga gacatgcaac cagagcgtga tcacctacga gaacaacacc      180
tgggtgaacc agacctacgt gaacatcagc aacaccaact cgccgctgg ccagagcgtg       240 gtgtctgtga agctggccgg caacagcagc ctgtgccctg tgtccggctg gccatctac      300 agcaaggaca cagcgtgcg gatcggcagc aagggcgacg tgttcgtgat ccgggagccc       360
ttcatcagct gcagcccct ggaatgccgg accttcttcc tgacccaggg ggccctgctg       420
aacgacaagc acagcaacgg caccatcaag gacagaagcc cctaccggac cctgatgagc      480
tgccccatcg gcgaggtgcc cagccccta acagcagat cgagtccgt ggcttggagc         540 gcctctgcct gcacgacgg catcaactgg ctgacaatcg gcatcagcgg ccctgataac       600
ggcgctgtgc ccgtgctgaa gtacaacggc atcatcaccg acacaatcaa gagctggcgg     660
aacaacatcc tgcggaccca ggaatccgag tgcgcctgcg tgaacggcag ctgcttcacc    720
gtgatgaccg acgccctag caatggccag gccagctaca agatcttccg gatcgagaag     780
ggcaagatcg tgaagtccgt ggagatgaac gcccccaact accactacga ggaatgcagc    840 tgctacccg acagcagcga gatcacctgt gtgtgccggg acaactggca cggcagcaac     900
agaccctggg tgtccttcaa ccagaatctg gaataccaga tcggctacat ttgcagcggc     960
atcttcggcg acaaccccag acccaacgac aagaccggaa gctgcggccc tgtgtctagc   1020
aacggggcca acggcgtgaa gggcttcagc ttcaagtacg gcaatggcgt gtggatcggc    1080
cggaccaaga gcatcagcag ccggaacggc ttcgagatga tctgggaccc caacggctgg    1140
```

```
accggcaccg acaacaactt cagcatcaag caggacatcg tgggcatcaa cgagtggagc    1200
ggctacagcg gcagcttcgt gcagcaccct gagctgaccg gcctggactg catccggccc    1260
tgcttttggg tggagctgat cagaggcaga cccaaagaga acaccatctg gaccagcggc    1320
agcagcatca gcttttgcgg cgtgaacagc gacaccgtgg gctggtcttg gcccgatggg    1380
gccgagctgc ccttcaccat cgacaagtga ggcgccgaga attcttaatt aa            1432

<210> SEQ ID NO 5
<211> LENGTH: 1698
<212> TYPE: DNA
<213> ORGANISM: Influenza A virus

<400> SEQUENCE: 5
atgaaaacca tcatcgccct gagctacatc ctgtgcctgg tgttcgccca gaagctgccc     60
ggcaacgaca acagcaccgc caccctgtgc ctgggccacc acgccgtgcc caacggcacc    120
atcgtcaaaa ccattaccaa tgatcagatc gaggtgacca cgccaccga gctggtgcag     180 agcagcagca ccggcggcat ctgcgacagc ccccaccaga tcctggacgg cgagaactgc    240
accctgatcg acgctctgct cggcgaccct cagtgcgacg gcttccagaa caagaagtgg    300
gacctgttcg tcgagcgcag caaggcctac agcaactgct acccctacga cgtgcccgac    360
tacgccagcc tccgctccct ggtcgcctcc agcggcaccc tggagttcaa cgacgagagc    420
ttcaactgga ccggcgtgac ccagaacggc accagcagca gctgcaagcg ccgcagcaac    480
aacagcttct tcagccgcct gaactggctg acccacctga gttcaagta ccccgccctg     540 aacgtgacca tgcccaacaa tgagaaattc gacaagctgt acatctgggg cgtgcaccac    600
cccgtgaccg acaacgacca gatcttcctg tacgcccagg ccagcggccg catcaccgtg    660
agcaccaagc gcagccagca gaccgtgatc cccaacatcg gcagccgccc caggatccgc    720
aacatcccca gccgcatcag catctactgg accatcgtga gcccggcga catcctgctg    780 atcaactcca ccggcaacct gatcgccccc aggggctact tcaagatccg cagcggcaag    840
agcagcatca tgcgcagcga cgcccccatc ggcaagtgca acagcgagtg catcaccccc    900
aacggcagca tccccaacga caagcccttc cagaacgtga accgcatcac ctacggagcc    960
tgtccccgct acgtgaagca gaacaccctg aaactggcta ccggcatgcg gaacgtgccc   1020
gagaagcaga cccggggcat cttcggggcc atcgccggct tcatcgagaa cggctgggag   1080
ggcatggtgg acgggtggta tggcttccgc caccagaact ccgagggcat cggccaggcc   1140
gccgacctga agagcaccca ggccgccatc aaccagatca cggcaagct gaaccgcctg   1200 atcggcaaga ccaacgagaa gttccaccag atcgagaagg agtttagcga ggtcgagggc   1260
cgcatccagg acctggagaa gtacgtggag gacaccaaga tcgacctgtg gagctacaac   1320
gccgagctgc tggtcgccct ggagaaccag cacaccatcg acctgaccga cagcgagatg   1380
aacaagctgt tcgagcgcac caagaagcag ctgcgcgaga cgccgagga catgggcaac   1440 ggctgcttca agatctacca caagtgcgac aacgcctgca tcggctccat ccgcaacggc   1500
acctacgacc acgacgtgta ccgcgacgag gccctgaaca accgcttcca gatcaagggc   1560
gtggagctga gagcggcta caaggactgg atcctgtgga tcagcttcgc tatcagctgc   1620
ttcctgctgt gcgtggccct gctgggcttc atcatgtggg cctgccagaa gggcaacatc   1680
cgctgcaaca tctgcatc                                                 1698

<210> SEQ ID NO 6
<211> LENGTH: 1410
```

```
<212> TYPE: DNA
<213> ORGANISM: Influenza A virus

<400> SEQUENCE: 6
atgaacccca accagaagat catcaccatc ggatccgtca gcctgaccat ctccaccatc      60 tgcttttca tgcagatcgc catcctgatc accaccgtga ccctgcactt caagcagtac     120
gagttcaaca gccccccaa caaccaggtc atgctgtgcg agcccaccat catcgagcgc     180
aacatcaccg agatcgtgta cctgaccaac accaccatcg agaaagagat ctgccccaag     240
ctggccgagt accgcaactg gtccaagccc cagtgcaata tcacaggctt cgccccttc     300 agcaaggaca acagcatccg cctgagcgct ggaggggaca tctgggtcac ccgcgagccc     360
tacgtgagct gcgaccccga caagtgctac cagttcgccc tcggacaggg gaccacactg     420
aataacgtcc acagcaacga caccgtgcac gaccgcaccc cctaccgcac cctgctgatg     480
aacgagctgg gcgtgccctt ccacctgggc accaagcagg tctgcatcgc ctggtccagc     540
agcagctgcc acgacggcaa ggcctggctg cacgtgtgcg tgaccggcga cgacaagaac     600
gccaccgcca gcttcatcta caacggccgc ctggtggaca gcatcgtgag ctggtccaaa     660
gagatcctgc gcacccaaga aagcgagtgc gtctgcatca acggcacctg caccgtggtg     720
atgaccgacg gcagcgcctc cggcaaggcc gacaccaaga tcctgttcat cgaagagggc     780
aagatcgtgc acaccagcac actgtccggc agcgcccagc acgtggaaga gtgcagctgc     840
tacccccgct acctgggcgt gcgctgcgtg tgccgcgaca actggaaggg cagcaaccgc     900
cccatcgtgg acatcaacat caaggactac tccatcgtga gcagctacgt gtgcagcggc     960
ctggtcggcg acacacccg caagaacgac agcagctcca gcagccactg cctggaccc    1020 aacaacgaag agggcggcca cggcgtgaag ggctgggcct tcgacgacgg caacgacgtg    1080
tggatgggcc gcaccatcag cgagaagctg cggagcggct atgagacatt caaggtgatc    1140
gagggctggt ccaaccccaa cagcaagctg cagatcaacc gccaggtgat cgtggaccgc    1200
ggcaaccgct ccggctacag cggcatcttc agcgtggagg gcaagtcctg catcaaccgc    1260
tgcttctatg tggagctgat tcgggggagg aaagaagaga ccgaggtcct ctggaccagc    1320
aacagcatcg tggtgttctg cggcaccagc ggcacctacg gcaccggcag ctggcccgac    1380
ggggccgaca tcaacctgat gcccatctga                                    1410
```

ALPHA-TOCOPHEROL-BASED ADJUVANTED SOLVENT FOR DNA VACCINES

FIELD OF INVENTION

The invention discloses a diluent or delivery system for DNA and RNA vaccines comprising an emulsion of tocol and esters hereof. Preparation of a pharmaceutical composition for the vaccination against infections and the hereby prepared vaccine and administration of said vaccines. The invention also discloses methods for immunizing an animal, including a human being, against an infectious disease and ways of administration of said vaccines.

GENERAL BACKGROUND (STATE OF THE ART)

Although DNA vaccines were developed more than 16 years ago, clinical trials preceding stage I and II in humans are rare. Three veterinary DNA vaccines however, have been licensed (Kurtzler M A & Weiner D B. DNA vaccines: ready for prime time? Nature rev 2008); one for West Nile Virus (in horse), one for Infectious Hematopoetic Necrosis virus in Salmon, one against Melanoma in dogs, and a plasmid for growth hormone releasing hormone in swine. This demonstrates that DNA vaccines/therapies can have good protective effects and that new DNA vaccines are not limited by the size of the animal or species. The great success with DNA vaccines observed for the murine model for first generation DNA vaccines did not translate well to humans, nonetheless; researchers have recently demonstrated protective antibodies levels by a single dose of gene gun administrated HA DNA vaccine to humans. Therefore, there is a future for improved DNA vaccines in human and veterinarian clinics.

"Nucleic acid immunization" or the commonly preferred name "DNA vaccines" are the inoculation of antigen-encoding DNA or RNA as expression cassettes or expression vectors, which may also be incorporated into viral delivery vectors with the purpose of inducing immunity to the gene product. Thus, in our definition of DNA vaccines we include all kinds of delivery systems for the antigen encoding naked DNA or RNA including viral vector-based delivery. The vaccine genes can be in form of circular plasmid or a linear expression cassette with just the key features necessary for expression (promotor, the vaccine gene and polyadenylation signal). Delivery systems may most often be naked DNA in buffer with or without adjuvant, DNA coupled to nanoparticles and/or formulated into adjuvant containing compounds or inserted into live viral or bacterial vectors such as Adenovirus, adeno-associated virus, alphavirus, poxviruses, herpes virus etc.

DNA vaccines hold great promise since they evoke both humoral and cell-mediated immunity, without the same dangers associated with live attenuated virus vaccines. In contrast to live attenuated virus vaccines DNA vaccines may be delivered to the same or different tissue or cells than the live virus that has to bind to specific receptors. The production of antigens in their native forms improves the presentation of the antigens to the host immune system. Unlike live attenuated vaccines, DNA vaccines are not infectious and cannot revert to virulence. DNA vaccines expressing influenza virus HA, NA, M, NP proteins or combinations of these have proven to induce immune responses comparable to that of a natural viral infection.

DNA vaccines offer many advantages over conventional vaccines. It can be produced in high amounts in short time, abolishing the need for propagation in eggs, it is cost-effective, reproducible and the final product does not require cold storage conditions, because DNA is stable and resistant to the extremes of temperature. All currently licensed inactivated vaccines are efficient at inducing humoral antibody responses but in general only live attenuated virus vaccines and DNA vaccines efficiently induce a cytotoxic cellular response as well. Moreover, The DNA vaccine's protein product is produced in vivo by the host cells believed to ensure more correct folding and glycosylation and presentation to the immune system than in vitro produced protein or glycoprotein immunogens.

DNA vaccines induce an immune response, which is comparable to the response acquired by natural virus infection by activating both humoral immunity to also native proteins or glycoproteins as well as cell-mediated immunity to intracellular processed immunogens (6, 30). The broad response to DNA vaccines is a result of the encoded genes being expressed by the transfected host cell, inducing both a Th1 and Th2 immune responses. The production of antigens in their native form improves the presentation of the antigens to the host immune system.

The standard DNA vaccine consist of a vector backbone with the gene of interest cloned into a bacterial plasmid engineered for optimal expression in eukaryotic cells. Essential features include; an origin of replication allowing for production in bacteria, a bacterial antibiotic resistance gene allowing for plasmid selection in bacterial culture during production of plasmid DNA, a strong constitutive promotor for optimal expression in mammalian cells (e.g. promoters derived from cytomegalovirus (CMV) or simian virus provide the highest gene expression), a polyadenylation sequence to stabilise the mRNA transcripts, such as bovine growth hormone (BHG) or simian virus polyadenylation signals, and a multiple cloning site for insertion of an antigen gene.

An intron A sequence improves expression of genes remarkably and may be included in the expression plasmid backbone. Many bacterial DNA vaccine vectors contain unmethylated cytidinephosphate-guanosine (CpG) dinucleotide motifs that may help eliciting adjuvanting innate immune responses in the host. In recent years, there have been several approaches to enhance and customise the immune response to DNA vaccine constructs (2nd generation DNA vaccines). For instance, dicistronic vectors or multiple gene expressing plasmids have been used to express two genes simultaneously. Specific promoters have been engineered that restrict gene expression to certain tissues, and cytokine/antigen fusion genes have been constructed to enhance the immune response. Furthermore, genes may be codon optimised for optimal gene expression in the mammalian host and naïve leader sequences may be substituted with stronger optimised leaders increasing translation efficiency.

The two most common types of naked DNA vaccine administration have so far been saline or PBS (phosphate buffered saline) needle injection of naked DNA and gene gun DNA inoculations (DNA coated on solid gold beads administrated with helium pressure). A saline intra muscular injection of DNA preferentially generates a Th1 IgG2a response while gene gun delivery tends to initiate a more Th2 IgG1 response. Intramuscular injected plasmids are at risk of being degraded by extracellular deoxyribonucleases, however, the responses induced are often more long-lived than those induced by the gene gun method. Vaccination by gene gun delivery of DNA, to the epidermis, was considered the most effective method of immunization, probably because the skin is a very immunogenic organ containing all the necessary cells types, including professional antigen presenting cells (APC), for eliciting both humoral and cytotoxic cellular immune responses (e.g. Langerhans and dendritic cells).

In 2003 electroporation of DNA was introduced as a way of improving transfection of mammalian cells with foreign DNA e.g. in cancer treatment. It is now a well recognized way of administration a naked DNA vaccine and one of the most efficient and most potent delivery methods so far. Electroporation, or electropermeabilization, is caused by an externally applied electrical field, which results in a significant increase in the electrical conductivity and permeability of the cell plasma membrane thereby subsequently transferring the administered DNA into the cells in the administered area. The organ targeted for the delivery with electroporation is most often muscle and/or skin. The disadvantages or challenges using needle and using electroporation is several. Intradermal injection require skills to perform and the vaccine is only deposited at the site where the needle tip ends up. In contrast, a needle-free jet delivery targets several layers of the skin reaching APC in different layers and do not require the same expert skills. In addition, needle's possess a risk for needle injury to the handler. More over the relatively time consuming process of both injection and electroporation may require immobilization of the animal and possible anaesthesia, access to electricity etc. Even with hand held cordless devices the technique delivers an electric pulse that may be painful. Because of the very efficient transfection obtained by moving plasmid DNA by the electric field during electroporation there is a fear that such foreign plasmid DNA may have increased possibility of integrating into the host chromosomes. This would become a safety risk. In contrast, a method that delivers the DNA vaccine fast without the need for needles and electroporation would be a considerable advantage and be an improvement in animal health and safety for the person who vaccinates. However, until now the most efficient mode of deliver DNA vaccine for optimal immune induction has been injection either intramuscular or intradermal followed by electroporation. The use of adjuvants is most wanted for DNA vaccines; however, such attempts has been mostly by codelivery of adjuvanting compounds such ad cytokines or plasmids encoding cytokines e.g. GM-CSF, IL-15.

SUMMARY OF THE INVENTION

The present invention discloses that DNA vaccine plasmids can be dissolved and diluted in a special buffer without precipitation. The diluent contain E-vitamin or -derivates that may help adjuvanting DNA without addition of cytokines or plasmids encoding cytokines. The DNA can be delivered in the diluent e.g. to the skin e.g. using needle-free devices already in use for protein vaccine delivery to the skin of pigs. However, it may also be delivered in other possible ways like injection. We have found that such delivery of DNA vaccines in the diluent is as efficient in inducing immunity as the use of injection followed by electroporation but much more convenient, easy and safe, thus allowing for mass vaccination of animals such as pigs birds and humans.

DETAILED DISCLOSURE OF THE INVENTION

The present invention discloses a diluent or delivery system for nucleic acid vaccines comprising an emulsion of tocol and esters hereof. A preferred tocol is α-tocopherol and esters such as α-tocopherol acetate or the racemat dl-α-tocopherol acetate.

The diluent or delivery system can further comprise an emulsifier chosen from the group of non-ionic surfactants, such as polyoxyethylene sorbitan mono-oleate (polysorbate), polyoxyethylene monolaurate, polyoxyethylene fatty acid esters, such polyoxyethylene stearate, polyoxyalkyl ethers, such as polyoxyethylene cetyl ether, polyoxyethylene castor oil derivatives, polyvinylpyrrolidone, polyvinyl alcohol, carboxymethylcellulose, lethicin and gelatin; anionic surfactants including salts of alkyl esters, such as sodium lauryl sulphate, cationic surfactants and amphoteric surfactants.

The diluent or delivery system of the invention can further comprise excipients such as buffers, electrolytes, surfactants, anti-foaming agents and polymer stabilisators. A preferred composition is where the buffer is disodiumphosphate/sodiumdihydrogenphosphate, the electrolyte is NaCl and the surfactant, anti-foaming agent and polymer stabilisator is polydimethylsiloxan (PDMS).

The invention also discloses an adjuvant consisting of the above diluent or delivery system additionally comprising an immunomodulator or immunostimulator.

The invention further discloses the use of a diluent or delivery system according invention for the preparation of a pharmaceutical composition for the vaccination against infections and the hereby prepared vaccine for immunizing an animal, including a human being.

The invention also discloses methods for immunizing an animal, including a human being, against an infectious disease by administration of a vaccine comprising the diluent or delivery system. Administration can be intramuscular or subcutaneous injection by injection with a syringe and needle or by a needle free jet injector.

Tocols are the basic unit of the tocopherols and tocotrienols. A hydroquinone with a saturated side chain.

Nucleic Acid Vaccines:

Nucleic acid vaccines are here defined as naked DNA or RNA, in solution for direct intramuscular or subcutaneous or intradermal injection with or without electroporation or coupled to particles, e.g. gold beads for gene gun administration. The DNA or RNA can be linear containing only a promoter, the vaccine genes that can be influenza genes and a polyadenylation signal or this expression cassette can be inserted into an expression plasmid.

Codon optimization of vaccine genes is the complete exchange of the virus codons to those of highly expressed human genes and therefore mammalian genes that include swine. Codon optimization do not change the encoded amino acids of the protein antigens encoded but may increase the eukaryotic protein expression in mammalian cells. Since genes of highly expressed human proteins has a high content of C and G there are an increased possibility of generating both immune stimulatory GpG motofs but also immune inhibitory GC sequences. Genes engineered using codon optimization are called "humanized" genes and are frequently used in DNA vaccines to enhance expression and immunogenicity.

An adjuvant is defined as a substance that non-specifically enhances the immune response to an antigen in this case the injected DNA. Depending on the nature of the adjuvant it can promote a cell-mediated immune response, a humoral immune response or a mixture of the two. When used as a vaccine adjuvant an antigenic component is added to the adjuvant solution.

An adjuvant (from latin adjuvare, to help) can be defined as any substance that when administered in the vaccine serves to direct, accelerate, prolong and/or enhance the specific immune response to an antigen e.g. the DNA. Adjuvants has been divided into two major categories either delivery systems or immunomodulators/immunostimulators. The delivery system can e.g. be emulsions, polystyrene particles, niosomes, ISCOMS, virosomes, microspheres, or surfactant-like liposomes, which are vesicles made up of lipid bilayers.

The present invention discloses a water based diluent, adjuvant and delivery system that surprisingly enhances the uptake and/or expression of the injected DNA. The delivery system is an emulsion of tocol and esters hereof as well as α-tocopherol (5,7,8-trimethyltocol; vitamin-E) and esters hereof. A preferred emulsion is α-tocopherol acetate and more preferred the racemat dl-α-tocopherol acetate.

To enhance the stability and optimize the viscosity of the emulsion (an oil-in-water or water-in-oil solution) an emulsifier is needed. Suitable emulsifiers can be chosen from the group of non-ionic surfactants, such as polyoxyethylene sorbitan mono-oleate (polysorbate), polyoxyethylene monolaurate, polyoxyethylene fatty acid esters, such polyoxyethylene stearate, polyoxyalkyl ethers, such as polyoxyethylene cetyl ether, polyoxyethylene castor oil derivatives, polyvinylpyrrolidone, polyvinyl alcohol, carboxymethylcellulose, lethicin and gelatin; anionic surfactants including salts of alkyl esters, such as sodium lauryl sulphate; cationic surfactants and amphoteric surfactants.

Besides water the diluent or delivery system can have further excipients such as buffers, electrolytes, surfactants, anti-foaming agents and polymer stabilisators.

Any pharmaceutical compatible buffer system can be used. A preferred buffer comprises disodiumphosphate/sodiumdihydrogenphosphate.

A preferred electrolyte normally used in isotonic solvents is NaCl.

A well known agent that works well as surfactant, anti-foaming agent and polymer stabilisator is polydimethylsiloxan (PDMS) also known as Simiticon or simethicon.

The invention also pertains to a method for immunizing an animal, including a human being comprising administering to the animal a vaccine composition of the invention as described above.

The manner of application may be varied widely. Any of the conventional methods for ad-ministration of a vaccine in the diluent are applicable. These are believed to include, parenterally, by injection or the like. The dosage of the vaccine will depend on the route of administration and will vary according to the age and the size of the individual to be vaccinated.

Administration of the diluent or delivery system or adjuvant in a vaccine can be done with a traditional syringe needle based injection. The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 5000 μg, such as in the range from about 1 μg to 300 μg, and especially in the range from about 10 μg to 100 μg. Suitable regimens for initial administration and booster shots are also variable but are typified by an initial administration followed by subsequent inoculations or other administrations.

The vaccines are conventionally administered parenterally, by injection, for example, either intracutaneously, intradermally, subcutaneously or intramuscularly. In many instances, it will be necessary to have multiple administrations of the vaccine. Especially, vaccines can be administered to prevent an infection with virulent virus or bacteria and/or to treat established infection. When administered to prevent an infection, the vaccine is given prophylactically, before definitive clinical signs or symptoms of an infection are present. When given to treat an infection, the vaccine is given therapeutically, after the infection is established to limit further spread of the virus, prevent infection of new cells and to stimulate elimination of the virus infected cells or bacteria.

Administration by a needle free jet injector is a new and preferred way of administration. A jet injector is a type of medical injecting syringe that uses a high-pressure narrow jet of the injection liquid instead of a hypodermic needle to penetrate the epidermis. It is powered by compressed air or gas, either by a pressure hose from a large cylinder, or from a built-in gas cartridge or small cylinder. Jet injectors are used for mass vaccination e.g. of pigs, and as an alternative to needle syringes to inject medicine drugs other than vaccines.

Several needle free jet delivery systems of protein vaccines are on the market. MDS Vet produces IDAL (intradermal application liquids) for pigs, the PharmaJet ID or PharmaJet IM or Tropis or DSJI from Pharmajet and Biojector from Bioject are used for humans.

An example of nucleic acid vaccine comprising the delivery system described herein is an influenza A vaccine comprising the influenza genes NP and M from H1N1 1918, HA and NA from H1N1v 2009 and HA and NA from H2N3 1968. In a preferred embodiment, the DNA or RNA codons are optimized ("humanized") e.g. the DNA sequence for haemagglutinin and neuraminidase and matrix and nucleoprotein is changed so the sequence coding for said proteins is changed to be optimally expressed in mammalian cells. An example of use of such a vaccine with the disclosed delivery system is described in the examples with the following nucleic acid sequences:

| Influenza A nucleic acid | SEQ ID NO |
|---|---|
| NP from 1918 H1N1 | 1 |
| M from 1918 H1N1 | 2 |
| HA from 2009 H1N1v | 3 |
| NA from 2009 H1N1v | 4 |
| HA from 1968 H3N2 | 5 |
| NA from 1968 H3N2 | 6 |

FIGURE LEGENDS

FIG. 1. (a) H1N1pdm09 HA-specific IgG and (b) H3N2 1968 HA-specific IgG in rabbit sera post vaccination were measured by ELISA. Arrows indicate vaccination time points. Group A was immunized by i.d.+EP with influenza genes inserted into pSSI standard expression vector. Group B was immunized by IDAL with influenza genes inserted into pSSI vector, premixed with Diluvac®Forte. Thus, similar high antibody response was obtained in rabbits whether immunized by i.d: injection of DNA in PBS followed by EP (Gr.A) or by needle-free delivery of DNA in Diluvac®Forte (Gr.B). Group C was immunized by IDAL with influenza genes inserted into NTC8385-VA1 vector backbone and premixed with Diluvac®Forte. Group D was immunized by IDAL with influenza genes inserted into the NTC9385R vector, and premixed with Diluvac®Forte. Thus, similar IgG antibody response was obtained from three different plasmid backbones when the DNA was diluted in Diluvac®Forte and delivered with needle-free IDAL (Gr.B, C and D).

FIG. 2. DNA vaccine induced antibodies were measured in an HI assay and the HI titers are given as the geometric mean titer. The ability of the DNA vaccine-induced antibodies to react against H1N1pdm09 are seen in (a). The ability to cross-react with the antigentically different swine H1N1 (H1N1-2007) were also measured (b). Arrows indicate vaccination time points. Group A is immunized by i.d.+EP with influenza genes inserted into pSSI vector. Group B is immunized by IDAL with influenza genes inserted into pSSI vector, premixed with Diluvac®Forte. Group C is immunized by IDAL with influenza genes inserted into NTC8385-VA1 vector, premixed with Diluvac®Forte. Group D is immunized by IDAL with influenza genes inserted into NTC9385R vector, premixed with Diluvac®Forte. Thus, the DNA vaccine groups induced similar functional HAI titers whether the DNA was diluted in PBS and delivered by i.d. needle followed by EP (Gr.A), or if the DNA was diluted in Diluvac®Forte and delivered by needle-free IDAL (Gr.B). Similar HAI titers were induced when the influenza genes were inserted into three different plasmid backbones, diluted in Diluvac®Forte and delivered with needle-free IDAL (Gr. B, C and D).

FIG. 3. Dose-titration response in influenza DNA vaccinated pigs. IgG responses measured by ELISA against recombinant HA and NA protein, homologous to the DNA vaccine (a-c). In addition, the three vaccinated groups also developed serum IgG responses against vaccine non-homologous proteins; rec. HA, rec. NP and the M2e ectodomain peptide (d-f).

FIG. 4. Hemagglutination inhibition (HI) antibody response in DNA vaccinated pigs. HI antibody responses were measured against the human isolates H1N1v A/California/07/09 and H3N2 A/Aichi/02/68, homologous to the vaccine, (a and b). HI antibody responses were also measured against two isolates from swine, H1N2 A/swine/DK/10525/2008 and H1N1v A/swine/DK/10409/2013 (c and d).

FIG. 5. Influenza neutralizing activity in DNA vaccinated pigs. Neutralizing activity against the human isolates H1N1v A/California/07/09, homologous to the vaccine, were observed in animals from vaccinated group 3-5, at 2 weeks after 2nd vaccination, day 35 (a). The kinetics of the neutralizing response was tested for two pigs, receiving different doses of vaccine (b).

EXAMPLE 1

Construction of Expression Vectors

Influenza DNA vaccine genes were designed from nucleotide sequences published in GenBank (1918 NP: A/Brevig Mission/1/18(H1N1) AY744935, 1918 M: A/Brevig Mission/1/18(H1N1) AY130766, 2009 HA: A/California/04/2009(H1N1)pdm09 ACP41105, 2009 NA: A/California/04/2009(H1N1)pdm09 ACP41107, 1968 HA: A/Aichi/2/1968 (H3N2) AB295605, 1968 NA: A/Aichi/2/1968(H3N2) AB295606). The genes were made synthetically and designed to include the appropriate restriction enzymes and Kozak sequence (GCCACC), −1 base upstream from the start codon, for efficient cloning and transcription in the pSSI (Statens Serum Institut, DK), NTC8385-VA1 (Nature Technologies Corporation, Lincoln, Nebr., U.S.) [1] and NTC9385R (Nature Technologies Corporation, Lincoln, Nebr., U.S.) [1] expression vectors. The genes were synthesised using only codons from highly expressed human genes (codon optimised). By this, the nucleotide codons are altered (humanised), but the encoded amino acids are identical to those encoded by the viral RNA. The genes were further cloned individually into the pSSI, NTC8385-VA1 and NTC9385R expression vectors. The pSSI expression vector backbone contains kanamycin resistance gene, cytomegalovirus immediate-early promotor, intron A and polyadenylation signal. A tissue plasminogen activator (tPA) signal sequence is not included in the vector, since the influenza HA and NA genes carry their own signal sequences for secretory expression. The influenza NP and M genes have no need for secretory signals since they express internal proteins located inside the virus and the infected cells. The pSSI vaccine construct was produced in the *E. coli* strain DH5α, using kanamycin as selection antibiotic. Endotoxin free DNA purification of the vaccine clones were prepared by EndoFree Plasmid Giga Kit (QIAGEN). All inserts and vaccine clones were control sequenced. Both the NTC8385-VA1 and the NTC9385R vaccine constructs use antibiotic-free selection systems and have been produced in the HyperGRO™ fermentation process [2].

Vaccine Delivery Mode

The vaccine constructs were delivered in two different modes to the animals. 1) Intradermal (i.d.) needle injection of naked DNA in PBS, at two sites in shaved abdominal skin, followed by electroporation using OncoVet™ system (CytoPulse Sciencies/Cellectis, Romainville, France) over each injected area. 2) Needle-free i.d. injection using Intra-Dermal Application of Liquids (IDAL) immunization technique (MSD Animal Health, Summit, N.J., U.S.) distributed at two abdominal injection sites. Before IDAL injection, the vaccine constructs are premixed at 1:1 volume ratio with the Diluvac®Forte Adjuvant (Intervet/MSD), an aqueous oil-in-water emulsion based on dl-α-tocopherol (Vitamin E). Diluvac®Forte also contains DL-α-tocopheryl acetat, Polysorbate, Sodium chloride, Disodium phosphate/Potassium dihydrogen phosphate, Simithicone and water.

Immunizations

Ten-week-old female nulliparous New Zealand white rabbits were housed at Statens Serum Institute Animal Facility (Copenhagen, Denmark). Animal experiments were performed by certified animal handlers and according to the Animal Experimentation Act of Denmark and European Convention ETS 123. Acclimatization was at least 10 days prior to any experimental procedures. The rabbits were divided into four groups with four to five rabbits in each group and they were all vaccinated at week 0 and 3 of the experiment. Both vaccinations contained an identical mix formulation of 10 pmole of each influenza gene plasmid, see Table 1. Blood serum was collected before first vaccination (week 0), week 2, before second vaccination (week 3) and week 5. Thus the amount of plasmids delivered was adjusted to equal molar amounts because they had slightly different sizes.

Serum Antibody Determination by ELISA

ELISA plates (96 wells) were coated with 100 μl of recombinant influenza haemagglutinin protein antigen A/California/04/09(H1N1pdm09) or A/Aichi/2/1968 (H3N2) (Sino Biological, Beijing, China), 2 μg/ml in 50 mM carbonate buffer, overnight at 4° C. Wells were blocked with 2% skim milk powder in PBS buffer (1% BSA, 10% FCS and 1% Triton X-100) for one hour at room temperature. Plates were washed with 1% triton/PBS. Rabbit sera, diluted in 2% skim milk powder blocking buffer, were added and incubated for one hour at room temperature. The plates were again washed and incubated with horseradish peroxidase-conjugated anti-rabbit-IgG antibody (Sigma A1949) for one hour. Following washing, color was developed with TMB (Kem-En-Tec, Denmark) for 30 minutes and the reaction was stopped by adding 0.2M H2SO4. Absorbance was read at OD450 nm.

TABLE 1

Overview of rabbit vaccinations (week 0 and 3)

| Group | Numbers of rabbits | Delivery mode[a] | Plasmid-encoded immunogens | Expression vector | Dose/ vaccination | Diluent |
|---|---|---|---|---|---|---|
| A | 4 | i.d. needle + EP | HA(H1N1)pdm09 NA(H1N1)pdm09 NP(H1N1)1918 M(H1N1)1918 HA(H3N2)1968 NA(H3N2)1968 | pSSI | 10 pmole | PBS |
| B | 5 | IDAL | Same as Group A | pSSI | 10 pmole | Diluvac®Forte |
| C | 5 | IDAL | Same as Group A | NTC8385-VA1 | 10 pmole | Diluvac®Forte |
| D | 5 | IDAL | Same as Group A | NTC9385R | 10 pmole | Diluvac®Forte |

[a]EP: electroporation, IDAL: IntraDermal Application of Liquids

Haemagglutination Inhibitory Assay

Rabbit sera were treated with receptor destroying enzyme (RDE(II), Seiken, Japan) as described by the manufacturer. Viruses were titrated using a haemagglutination assay according to the protocols of the WHO [3] with 0.75% guinea pig red blood cells in U-bottom plates (U96 MicroWell Plates, Nunc) and incubated for one hour. Virus was standardized to 100% haemagglutination endpoint titer of 8 haemagglutination units (HAU). The haemagglutination inhibition (HI) assay was performed according to the protocols of the WHO [3] with 0.75% guinea pig red blood cells in U-bottom plates (U96 MicroWell Plates, Nunc) and the HI titers were read as the reciprocal of the last dilution of sera that completely inhibited haemagglutination.

Results from Rabbits Vaccinated with Influenza DNA Vaccine

Figure 1:
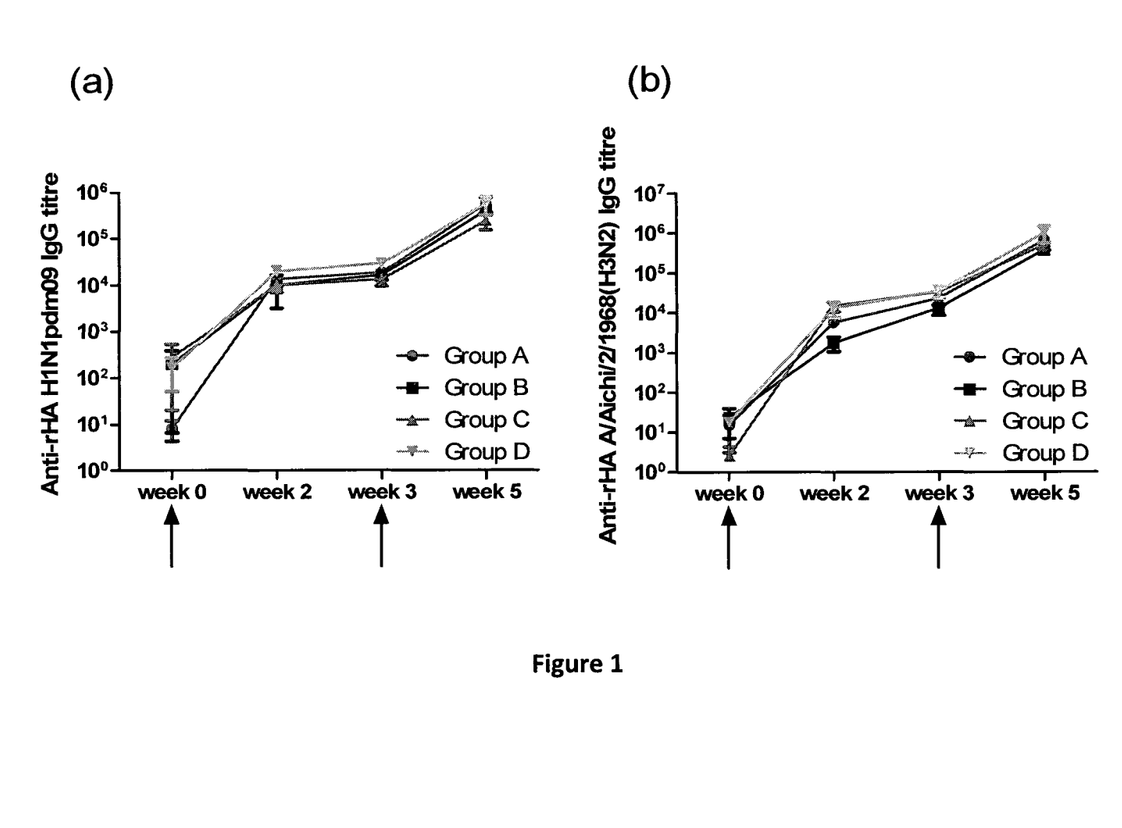
Figure 2:
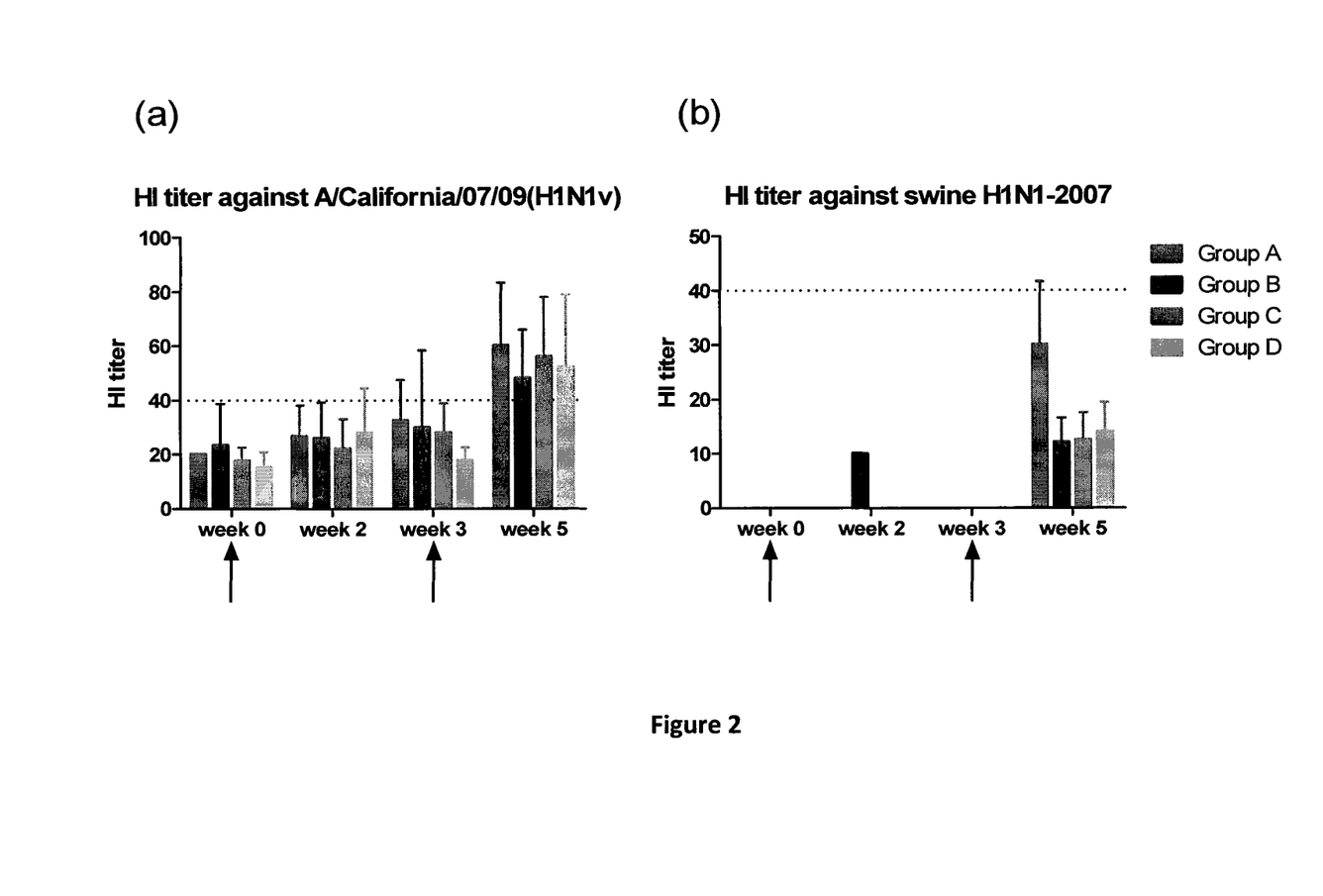

ELISA assay demonstrated high IgG specific serum antibodies against the vaccine components A/California/04/09 (H1N1) and A/Aichi/2/1968(H3N2). Specific IgG were observed two weeks post 1st vaccination in all vaccinated rabbit groups, to similar titers (FIG. 1). After 2nd vaccination at week three, the specific IgG titers increased further. It is possible that the antibody titers could have increased further at later time points, but the experiment was terminated after five weeks for practical reasons. Haemagglutination inhibition assay measures how well sera from vaccinated rabbits inactivate virus binding to red blood cells. HI antibody titers >40 corresponds to seroprotection rate after vaccination [4], and this was achieved in rabbit sera of all groups against homologous vaccine virus A/California/04/09(H1N1) after 2nd vaccination (FIG. 2a). To determine the cross reactivity obtained by using pandemic genes as DNA vaccine, we also tested HI titers against heterologous swine virus strain H1N1-2007 (FIG. 2b). All vaccinated rabbit groups did develop cross-reactive IgG against the antigentically different swine H1N1 after vaccination, but only to low HI titers. Heterologous human influenza strain H3N2 (A/Perth/16/2009) was also tested in the HI assay (FIG. 2c), however no vaccine-induced inhibition was observed for this strain in any rabbit group.

CONCLUSION

The data show that DNA immunizations with pandemic genes from three different virus strains (H1N1 2009, H1N1 1918, H3N2 1968) induce strong specific antibody response as detected in ELISA. The haemagglutination inhibition assay demonstrates that the vaccine also induce functional antibodies against both homologous virus strain to the vaccine and against heterologous swine influenza strain. The different mode of delivery gave similar immunological response. Diluting the plasmid DNA in Diluvac®Forte and deliver needle-free into the skin resulted in equal immune response as the present state of the art methodology with electroporation, but is much more user- and animal-friendly. The mix of DNA vaccine with the adjuvant Diluvac®Forte was possible with several different plasmid backbones and resulted in similar immunological response. The mixing of naked DNA with Diluvac®Forte resulted in a homogenous solution suitable for the needle-free delivery without any precipitation of DNA.

EXAMPLE 2

Pigs Vaccinated with Influenza DNA Vaccine

Figure 3:
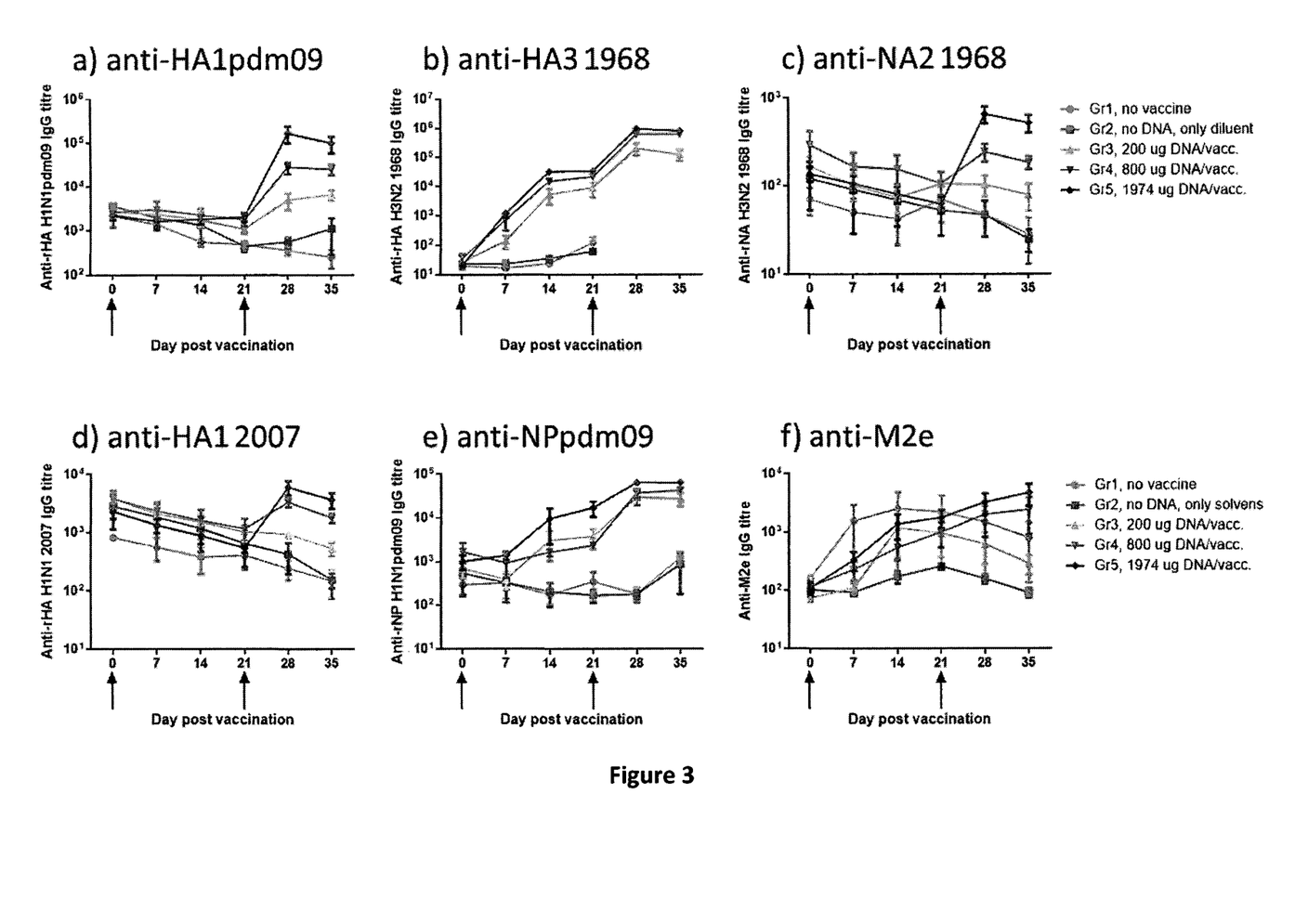
Figure 4:
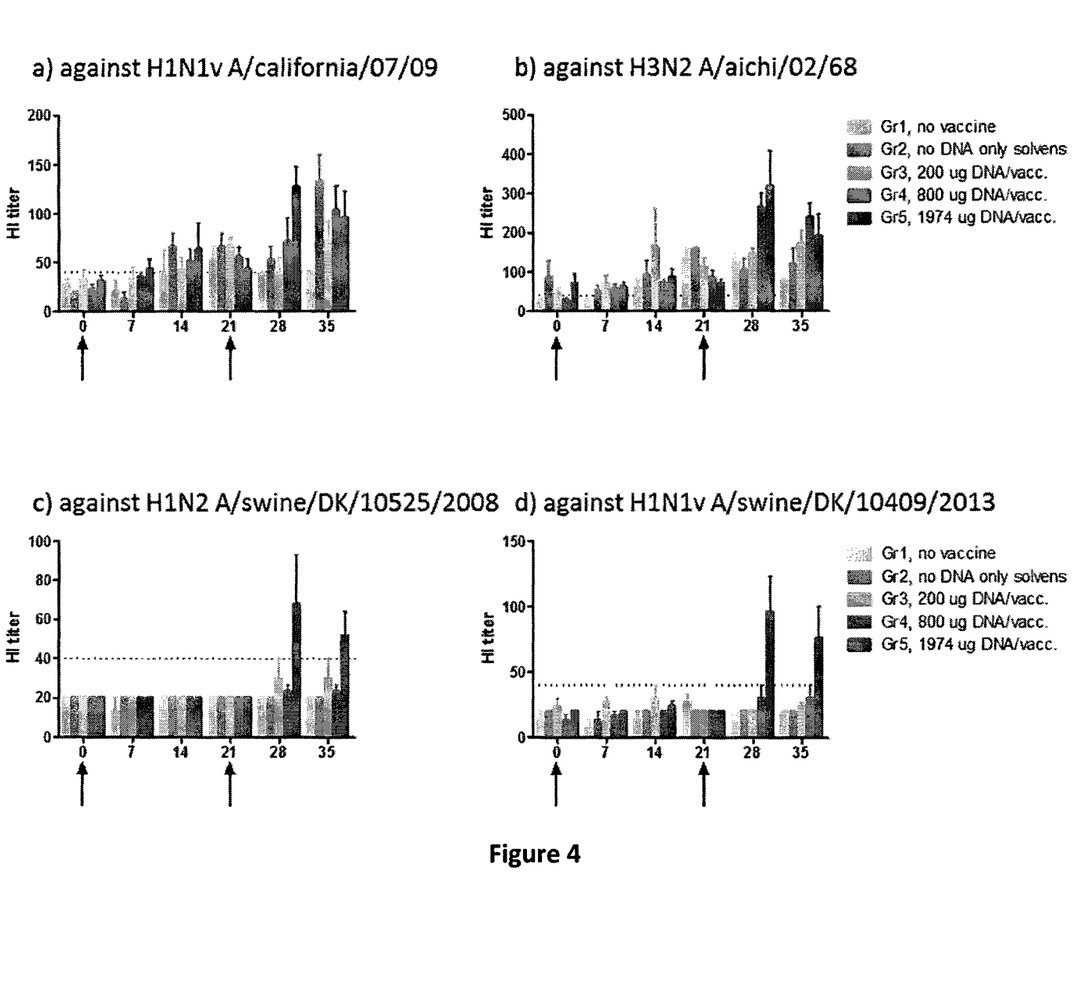
Figure 5:
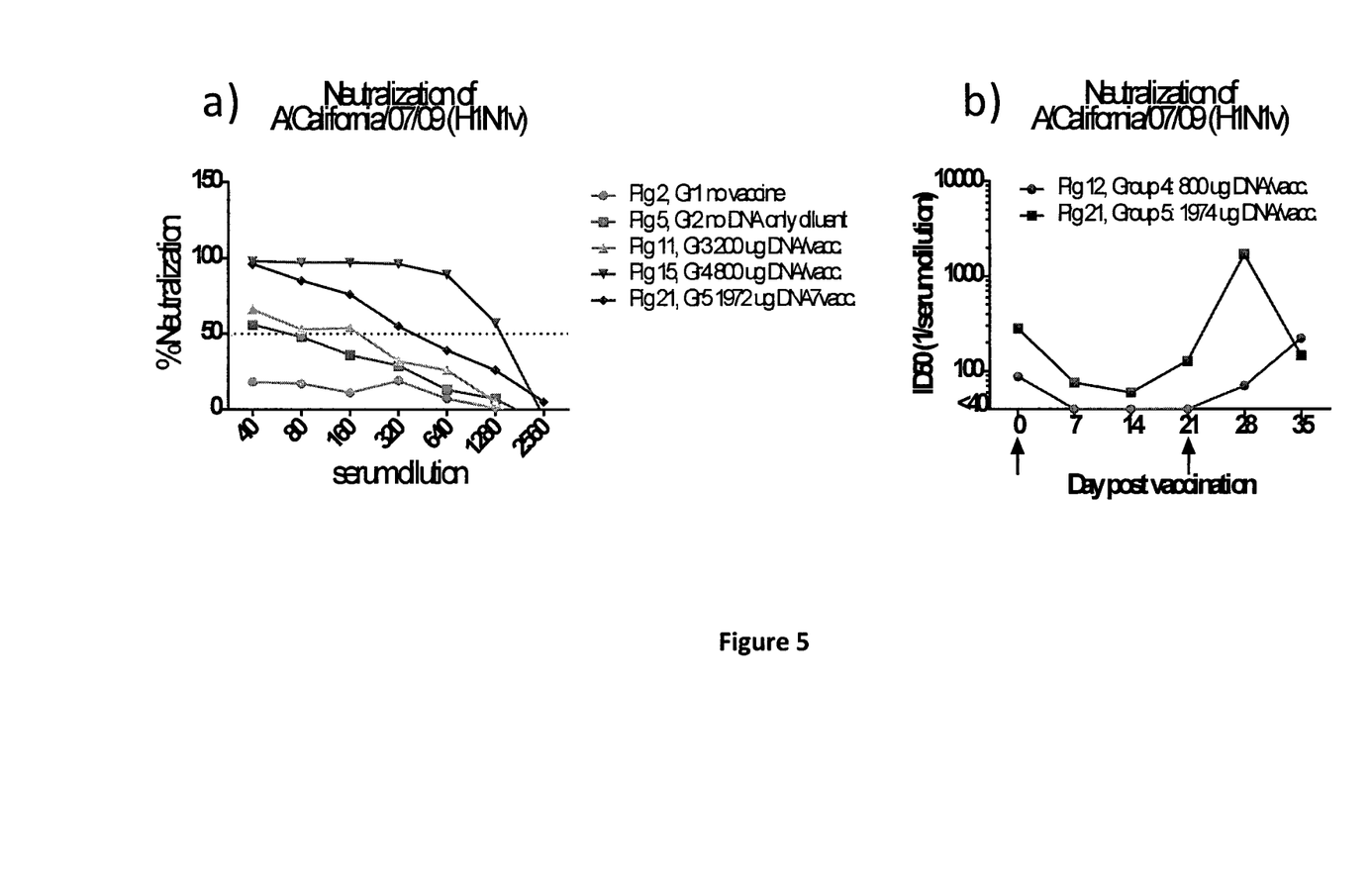

Three groups (group 3-5) of 5-6 pigs were immunized twice (see arrows), three weeks apart, with different doses of the same DNA based influenza vaccine consisting of HA+NA genes from H1N1pdm09, HA+NA genes from 1968 H3N2 and NP+M genes from 1918 H1N1 viruses. Two groups were used as control groups; group 1 received nothing and group 2 received only the α-tocopherol-based aqueous solution (Diluvac Forte®, MSD Animal Health) which the vaccine constructs were premixed with for practical use of the IDAL® delivery device. All three vaccinated groups (group 3-5) developed detectable serum IgG responses measured by ELISA against recombinant HA and NA protein, homologous to the DNA vaccine (FIG. 3a-c). In addition, the three vaccinated groups also developed serum IgG responses against vaccine non-homologous proteins; rec. HA, rec. NP and the M2e ectodomain peptide (FIG. 3d-f). HI antibody responses were measured against the human isolates H1N1v A/California/07/09 and H3N2 A/Aichi/02/68, homologous to the vaccine, (FIGS. 4a and b). HI antibody responses were also measured against two isolates from swine, H1N2 A/swine/DK/10525/2008 and H1N1v A/swine/DK/10409/2013 (FIGS. 4c and d). Neutralizing activity against the human isolates H1N1v A/California/07/09, homologous to the vaccine, were observed in animals from vaccinated group 3-5, at 2 weeks after 2nd vaccination, day 35 (FIG. 5a). The kinetics of the neutralizing response was tested for two pigs, receiving different doses of vaccine (FIG. 5b). The neutralizing response seem to follow the development of specific IgG detected in ELISA (FIG. 3a). Maternal IgG seem to exist at day 0 at the 1st vaccination time point. These vain over time, but a 2nd vaccination at day 21 can boost the neutralizing response.

In summary, the influenza DNA vaccine has induce a serum IgG response against both influenza proteins homologous to the vaccine and influenza proteins not expressed by the vaccine, as measured by ELISA (see group 3-5). The antibody titers seem to correlate with the doses of the vaccine given to the different groups. The control groups, which did not receive the DNA vaccine (group 1 and 2), did not develop any influenza specific IgG response. Influenza DNA vaccinated animals develop a functional antibody response against virus isolates both homologous to the vaccine and non-homologous. Higher HI titer seem to correlate with animals receiving higher doses of the vaccine. The control groups (group 1 and 2) has in general no or low response.

REFERENCES

1. Williams, J. A., *Vector Design for Improved DNA Vaccine Efficacy, Safety and Production.* Vaccines, 2013. 1(3): p. 225-249.
2. Carnes, A. E. W., J. A., *Process for plasmid DNA fermentation.* U.S. Pat. No. 7,943,377, 2011.
3. *WHO Recommendations for Influenza Vaccine Composition* [http://www.who.int/influenza/vaccines/virus/en/].
4. Coudeville, L., et al., *Relationship between haemagglutination-inhibiting antibody titres and clinical protection against influenza: development and application of a bayesian random-effects model.* BMC Med Res Methodol, 2010. 10: p. 18.

The invention claimed is:

1. A delivery system, for nucleic acid vaccines comprising α-tocopherol acetate or the racemat dl-α-tocopherol acetate, an emulsifier chosen from the group of non-ionic surfactants, anionic surfactants, cationic surfactants and amphoteric surfactants, and excipient disodiumphosphate/sodiumdihydrogenphosphate.

2. The delivery system according to claim 1, further comprising NaCl.

3. The delivery system according to claim 1, further comprising polydimethylsiloxan (PDMS).

4. The delivery system according to claim 1, further comprising an immunomodulator or immunostimulator.

5. A nucleic acid vaccine for immunizing an animal, comprising the delivery system according to claim 1.

6. The nucleic acid vaccine according to claim 5, comprising the influenza genes NP and M from H1N1 1918, HA and NA from H1N1 2009, and HA and NA from H2N3 1968.

7. The delivery system according to claim 1, wherein said non-ionic surfactant is polyoxyethylene sorbitan monooleate (polysorbate), polyoxyethylene monolaurate, a polyoxyethylene fatty acid ester, a polyoxyalkyl ether, a polyoxyethylene castor oil derivative, polyvinylpyrrolidone, polyvinyl alcohol, carboxymethylcellulose, lethicin or gelatin.

8. The delivery system according to claim 7, wherein said non-ionic surfactant is polyoxyethylene stearate or polyoxyethylene cetyl ether.

9. The delivery system according to claim 1, wherein said anionic surfactant is a salt of an alkyl ester.

10. The delivery system according to claim 9, wherein said anionic surfactant is sodium lauryl sulfate.

11. The nucleic acid vaccine according to claim 5, wherein said animal is a human being.

* * * * *